(12) United States Patent
Black (10) Patent No.: US 12,133,832 B2
(45) Date of Patent: Nov. 5, 2024

(54) THERMALLY ISOLATED BLOOD CARRIER TRAY

(71) Applicant: BIOFRIDGE INC., Escondido, CA (US)

(72) Inventor: Jay Black, Escondido, CA (US)

(73) Assignee: BIOFRIDGE INC.

( * ) Notice: Subject to any disclaimer, the term of this patent is extended or adjusted under 35 U.S.C. 154(b) by 1074 days.

(21) Appl. No.: 16/987,007

(22) Filed: Aug. 6, 2020

(65) Prior Publication Data
US 2020/0360234 A1 Nov. 19, 2020

Related U.S. Application Data

(63) Continuation of application No. 16/011,605, filed on Jun. 18, 2018, now Pat. No. 10,736,817.
(Continued)

(51) Int. Cl.
*A61J 1/16* (2023.01)
*A01N 1/02* (2006.01)
(Continued)

(52) U.S. Cl.
CPC .............. *A61J 1/16* (2013.01); *A01N 1/0242* (2013.01); *A61M 1/0272* (2013.01); *A61M 1/0286* (2014.02); *A61M 5/44* (2013.01); *A61M 5/445* (2013.01); *A61J 1/10* (2013.01); *A61M 2205/3368* (2013.01); *A61M 2205/36* (2013.01);
(Continued)

(58) Field of Classification Search
CPC ...... A61M 5/445; A61M 5/44; A61M 1/0286; A61M 1/0272; A61M 2205/3368; A61M 2205/3633; A61M 2205/362; A61M 2205/3606; A61M 2205/36; A61J 1/16; A61J 1/10; A01N 1/0242
See application file for complete search history.

(56) References Cited

U.S. PATENT DOCUMENTS

| 2,264,442 A | 12/1941 | Norman |
| D136,305 S | 9/1943 | Teeter |
| (Continued) | | |

FOREIGN PATENT DOCUMENTS

WO WO-03089301 A1 * 10/2003 .......... A47J 37/1228

*Primary Examiner* — Dana Ross
*Assistant Examiner* — Kuangyue Chen
(74) *Attorney, Agent, or Firm* — Gary L. Eastman, Esq.; Eastman IP (57) ABSTRACT

A Thermally Isolated Blood Carrier Tray includes a main panel having a plurality of thermally isolated compartments attached thereto. The thermally isolated compartments are arranged in two separate matrices having a plurality of column and rows. Each thermally isolated compartment is thermally isolated from an adjacent thermally isolated compartment. Each thermally isolated compartment maintains its own heat transfer rate without being affected by an adjacent thermally isolated compartments heat transfer rate. The placement of several different storage units having different temperatures into the Thermally Isolated Blood Carrier Tray does not affect the heat transfer rate of any one storage unit in a thermally isolated compartment. The Thermally Isolated Blood Carrier Tray provides a steady and even heat transfer from the storage unit to bring the storage units to an appropriate temperature for storage or transportation.

20 Claims, 9 Drawing Sheets

Related U.S. Application Data (60) Provisional application No. 62/521,233, filed on Jun. 16, 2017.

(51) Int. Cl.
  *A61M 1/02* (2006.01)
  *A61M 5/44* (2006.01)
  *A61J 1/10* (2006.01)

(52) U.S. Cl.
  CPC .............. *A61M 2205/3606* (2013.01); *A61M 2205/362* (2013.01); *A61M 2205/3633* (2013.01)

(56) References Cited

U.S. PATENT DOCUMENTS

| | | | |
|---|---|---|---|
| D148,128 S | 7/1946 | Brottman | |
| D155,785 S | 11/1949 | Davis | |
| 2,515,514 A | 7/1950 | Jones | |
| 2,522,623 A | 9/1950 | Likes et al. | |
| 2,932,718 A | 4/1960 | Marster | |
| D188,018 S | 5/1960 | Alger | |
| D190,213 S | 4/1961 | Krausz | |
| 2,984,383 A * | 5/1961 | Arneson | B65D 71/0022 206/184 |
| D197,282 S | 1/1964 | Gusdorf | |
| D198,821 S | 8/1964 | Hoyle | |
| 3,186,556 A | 6/1965 | Forsstrom | |
| D206,510 S | 12/1966 | Waltz et al. | |
| 3,764,780 A | 10/1973 | Ellis | |
| D256,587 S | 8/1980 | Tatsumi | |
| 4,278,176 A | 7/1981 | Adams | |
| 4,281,768 A | 8/1981 | Sommers | |
| D285,692 S | 9/1986 | Albiez | |
| D297,677 S | 9/1988 | Conn | |
| 4,801,428 A | 1/1989 | Homolko et al. | |
| D325,975 S | 5/1992 | Grade et al. | |
| 5,230,524 A | 7/1993 | Jackson | |
| 5,306,896 A | 4/1994 | Glater | |
| 5,671,991 A | 9/1997 | Grant | |
| 5,806,943 A | 9/1998 | Dell et al. | |
| D440,987 S | 4/2001 | Okamoto et al. | |
| D450,820 S | 11/2001 | Breshears et al. | |
| D454,892 S | 3/2002 | Black et al. | |
| 6,523,840 B1 | 2/2003 | Koppes et al. | |
| D477,083 S | 7/2003 | Bromley | |
| D478,198 S | 8/2003 | Koppes et al. | |
| D501,807 S | 2/2005 | Williamson | |
| 6,897,413 B1 | 5/2005 | Wertheim | |
| 6,906,292 B2 | 6/2005 | Weinfield | |
| D525,592 S | 7/2006 | Nguyen | |
| D547,849 S | 7/2007 | Francisquini | |
| 7,276,208 B2 | 10/2007 | Sevigny et al. | |
| D568,258 S | 5/2008 | Adam | |
| D606,722 S | 12/2009 | Walter | |
| D615,724 S | 5/2010 | Girard | |
| D616,081 S | 5/2010 | Chiu | |
| D620,032 S | 7/2010 | Kristiansen et al. | |
| 7,799,283 B2 | 9/2010 | Jacobs | |
| D626,236 S | 10/2010 | Ninomiya et al. | |
| 7,910,067 B2 | 3/2011 | Knight et al. | |
| D635,655 S | 4/2011 | Chen et al. | |
| D649,092 S | 11/2011 | Durojaiye | |
| D649,732 S | 11/2011 | Muscara | |
| D655,880 S | 3/2012 | Giampavolo et al. | |
| D657,469 S | 4/2012 | Vilas | |
| 8,246,919 B2 | 8/2012 | Herchenbach et al. | |
| D693,742 S | 11/2013 | Fredendall et al. | |
| 8,591,838 B2 | 11/2013 | Bulow et al. | |
| 8,657,304 B1 | 2/2014 | Fredendall et al. | |
| D701,888 S | 4/2014 | Schumaker et al. | |
| D735,781 S | 8/2015 | Hwang et al. | |
| D737,343 S | 8/2015 | Rinderer et al. | |
| D762,743 S | 8/2016 | Fan | |
| D770,718 S | 11/2016 | Fredendall et al. | |
| D777,891 S | 1/2017 | Kubota et al. | |
| D807,929 S | 1/2018 | Feng | |
| 10,092,137 B1 | 10/2018 | Nelson | |
| 2001/0042743 A1 | 11/2001 | Faries | |
| 2003/0017084 A1 | 1/2003 | Dale et al. | |
| 2003/0215365 A1 | 11/2003 | Sevigny et al. | |
| 2003/0235735 A1 * | 12/2003 | Miyazawa | H01M 8/2457 429/514 |
| 2009/0036863 A1 * | 2/2009 | Smith | B29C 49/04 604/408 |
| 2016/0361231 A1 * | 12/2016 | Chou | A61J 1/1412 |
| 2018/0125752 A1 * | 5/2018 | Gerrish | A61J 1/10 |
| 2019/0030236 A1 * | 1/2019 | Okihara | A61M 5/008 |

* cited by examiner

THERMALLY ISOLATED BLOOD CARRIER TRAY

RELATED APPLICATIONS

This Utility Patent Application is a continuation of U.S. patent Ser. No. 16/011,605 filed on Jun. 18, 2018, which claims the benefit of priority to U.S. Provisional Patent Application Ser. No. 62/521,233 filed on Jun. 16, 2017.

FIELD OF INVENTION

The present invention relates generally to medical devices, and more particularly, but not exclusively, to blood temperature control apparatuses.

BACKGROUND OF THE INVENTION

In the United States, every two seconds that elapses a different person is in need of a blood transfusion. Blood cannot be artificially manufactured and can come only from human donations. As a result, over 15.7 million blood donations are made per year. The donated blood is collected, processed, and stored until required for use.

Donated blood is collected as whole blood, which consist of red blood cells, platelets, plasma and cryoprecipitate. Whole blood may be processed, stored, and used as is, or it may be separated into its component parts and then processed for storage and use. After processing, whole blood and red blood cells can be stored for up to 42 days at between two (2) and six (6) degrees Celsius. Platelets must be used within five days of collection. Plasma and cryoprecipitate may be stored in a frozen state for up to one year after collection.

As donated blood or blood components are refrigerated for storage, new units added to the cooler could potentially transfer their heat to nearby units as well as the cooled air, creating undesirable consequences for the refrigeration and storage process. Such heat transfer between units may negatively affect the storage life of the blood or blood components.

Donated whole blood, or the components thereof, is delivered from blood banks to hospitals in its stored state. Whole blood is delivered with a temperature between two (2) and six (6) degrees Celsius and plasma and cryoprecipitate are delivered frozen with a temperature below negative twenty (−20) degrees Celsius. For whole blood, cold blood may be transfused without any ill effect if administered at a slow rate. However, for rapid transfusions of a large volume of blood it is recommended that the blood be brought to an appropriate temperature to avoid any complications, such as hypothermia. Whole blood should never be rapidly brought to temperature in a water bath, in hot towels, or close to a heating device as this could lead to extensive hemolysis and serious transfusion reactions. The frozen plasma and cryoprecipitate must be thawed before use. Frozen plasma and cryoprecipitate may be thawed using water baths, but must be monitored to ensure precise control of the water temperature to ensure uniform thawing to avoid damage.

Blood warmers are available to raise the temperature of whole blood to an appropriate temperature for use. Blood warmers are typically limited to bringing to temperature a single unit of whole blood. The most common blood warmers now in use are in-line warmers, which are not adequate for rapid-transfusions of a large volume of blood at a high rate. The use of water baths for thawing plasma and cryoprecipitate requires constant monitoring as mentioned above. Additionally, the warming of multiple units of plasma and cryoprecipitate into a single water bath affects the heat transfer rate of the individual units. The addition of new frozen plasma and/or cryoprecipitate units into an existing water bath with partially thawed units will reduce the temperature of the water bath as the water bath equilibrates to a steady state temperature. The resulting lower temperature of the water bath may then lower the temperature of the partially thawed units while simultaneously raising the temperature of the frozen units. The use of a single water bath to thaw several units slows the overall heat transfer rate of each individual unit when compared to using a single water bath for a single unit.

Although, as explained above, the rate of heating blood for rapid, large-volume transfusions is a significant concern, insufficient attention has been paid to the cooling process. Since cold blood may be used without any negative effects in many transfusions, providing a more reliable way to cool blood or blood components and maintain a consistent temperature may have as significant an effect on transfusion success rate as improvements in heating blood. Additionally, storage lesion—biochemical and biomechanical changes to red blood cells which occur irregularly during storage—is a significant cause of poor transfusion outcomes regardless of the temperature at the time of transfusion. At the very least, a method or apparatus for thermally isolating individual units can reduce the risk and magnitude of quality degradation during the storage, transportation, and use of blood or blood components.

In light of the above, it would be advantageous to provide a blood carrier that is capable of thermally isolating individual compartments. It would further be advantageous to provide a blood carrier capable of warming or cooling multiple units simultaneously without affecting the heat transfer rates of the other units. It would further be advantageous to provide a blood carrier with which units of blood could be placed in a cooler and removed while minimizing effects on the temperature of the other units.

SUMMARY OF THE INVENTION

The Thermally Isolated Blood Carrier Tray provides a steady and even heat transfer to or from whole blood storage units, red cell storage units, platelet storage units, plasma storage units, or cryoprecipitate storage units (hereinafter referred collectively as "storage units") to bring the contents of the storage units to an appropriate temperature for storage or for use. The Thermally Isolated Blood Carrier Tray is capable of cooling multiple storage units simultaneously without affecting the heat transfer rates of other storage units, such that the introduction of a warm blood storage unit into the carrier tray will not thermally impact the other blood storage units already in the tray and at the desired temperature.

The Thermally Isolated Blood Carrier Tray includes a main panel having a plurality of thermally isolated compartments attached thereto. In a preferred embodiment, the thermally isolated compartments are arranged into two separate matrices having a plurality of column and rows. Each thermally isolated compartment is thermally isolated from an adjacent thermally isolated compartment. The placement of several different storage units having different temperatures into the Thermally Isolated Blood Carrier Tray does not affect the heat transfer rate of any one storage unit in a thermally isolated compartment. Each thermally isolated compartment and the storage unit housed within maintains its own heat transfer rate without being affected by an adjacent thermally isolated compartment and storage unit. The Thermally Isolated Blood Carrier Tray allows for the placement of storage units having different temperatures into the Thermally Isolated Blood Carrier Tray at different times to change its temperature to an appropriate temperature as determined by the surrounding environmental temperature without the need to determine the effects it would have on the overall heat transfer rate.

In an alternative embodiment of the Thermally Isolated Carrier Tray, the thermally isolated compartments are each removably attached to one another thereby allowing for the scaling of the Thermally Isolated Carrier Tray to accommodate any number of storage units. The removable attachment of the thermally isolated compartment allows for the scalability of the matrix of thermally isolated compartments, as well as to provide additional matrices of thermally isolated compartments as needed. The matrix of thermally isolated compartments may be configured to have as many rows and columns as desired for a particular purpose. The Thermally Isolated Carrier Tray may be modified to have additional main panels to provide additional structural support and thermal isolation as needed between each matrix of thermally isolated compartments.

The Thermally Isolated Carrier Tray as described herein includes a thermal mass that provides at least two important benefits. First, the thermal mass of the individual isolated compartments provides temperature stability when the storage unit, such as a cooler or refrigeration chest is opened and exposed to ambient air. Second, the thermal mass of the individual isolated compartment allows a warm storage unit to be placed in a lower temperature Thermally Isolated Carrier Tray compartment for cooling without any thermal impact on adjacent compartments. The thermal mass of the compartment more quickly cools the newly placed unit, while the thermal mass of the adjacent compartments prevents the units in those compartments from experiencing any noticeable thermal change.

BRIEF DESCRIPTION OF THE INVENTION

DETAILED DESCRIPTION OF THE FIGURES

Figure 1:
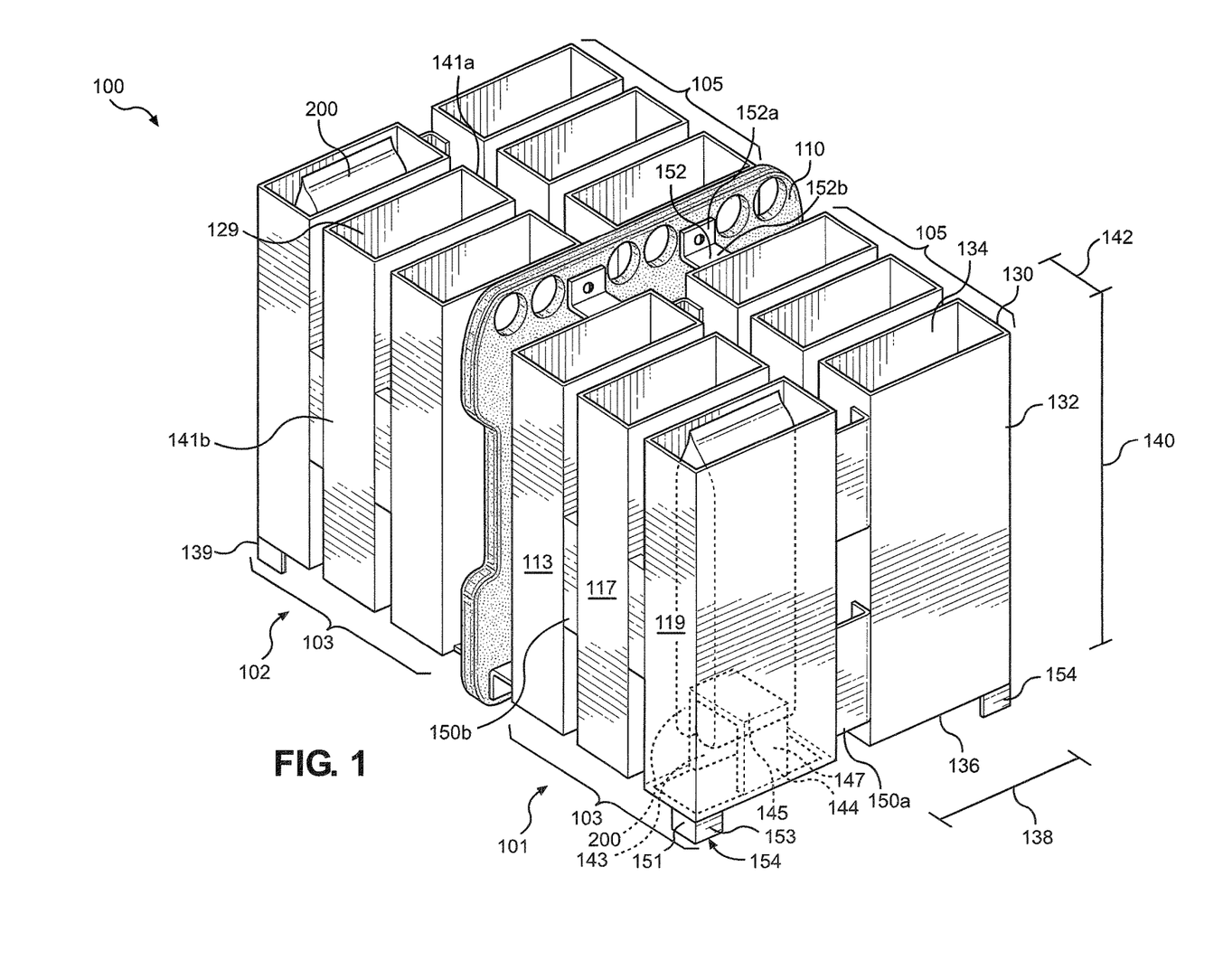
FIG. 1 is a front-left-top perspective view of a Thermally Isolated Blood Carrier Tray having a main panel with several individual thermally isolated compartments attached thereto.

Referring initially to FIG. 1, a Thermally Isolated Blood Carrier Tray is shown and generally designated 100. The Thermally Isolated Blood Carrier Tray 100, described in conjunction with FIGS. 2 and 3, includes a main panel 110 having a plurality of thermally isolated compartments 130 attached thereto. The thermally isolated compartments 130 are arranged into two separate matrices, specifically, a first matrix (101) and a second matrix (102) having a first row (103) and a second row (105).

Figure 2:
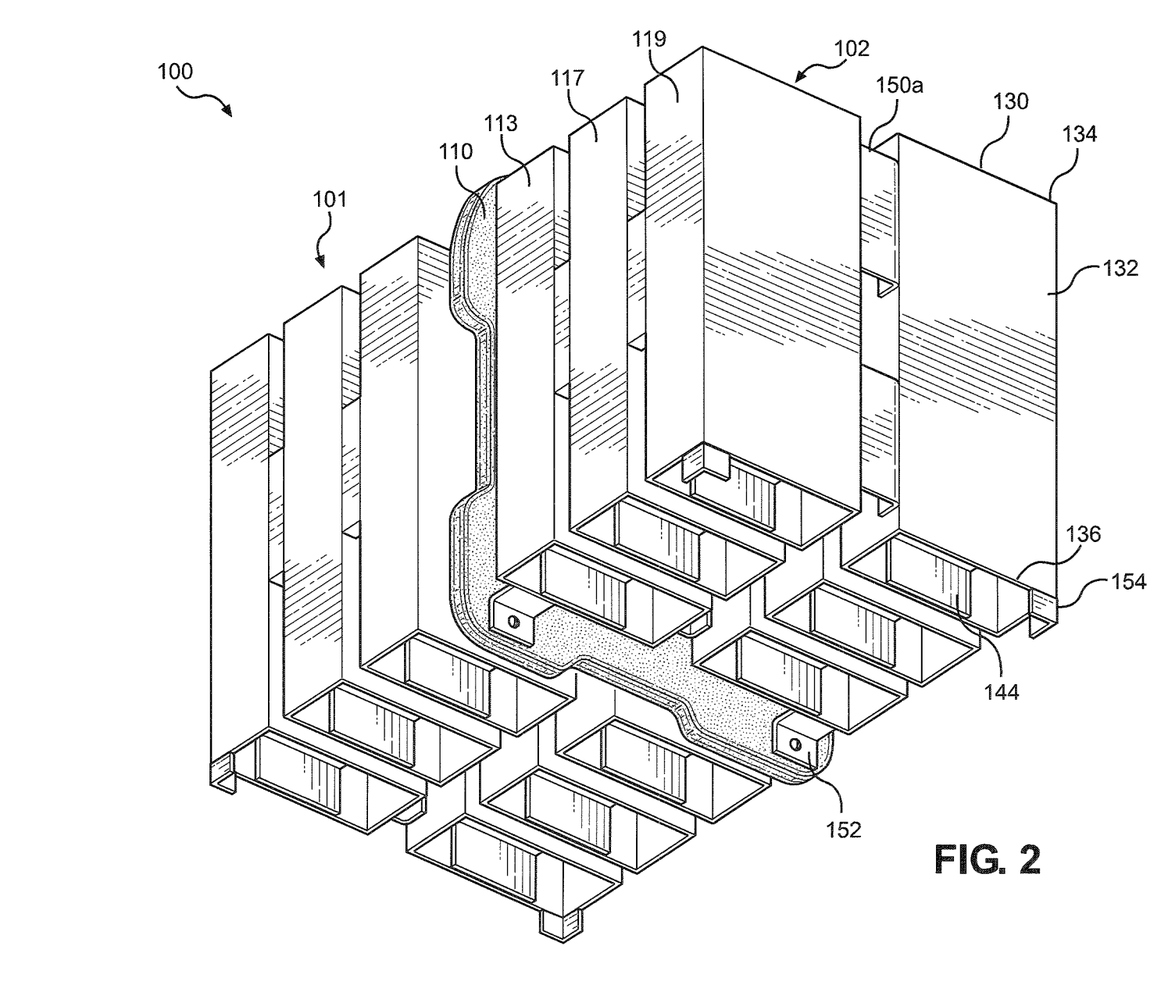
FIG. 2 is a back-right-bottom perspective view of the Thermally Isolated Blood Carrier Tray showing the thermally isolated compartments having an open bottom with a base attached within to provide a platform for a storage unit.
Figure 3:
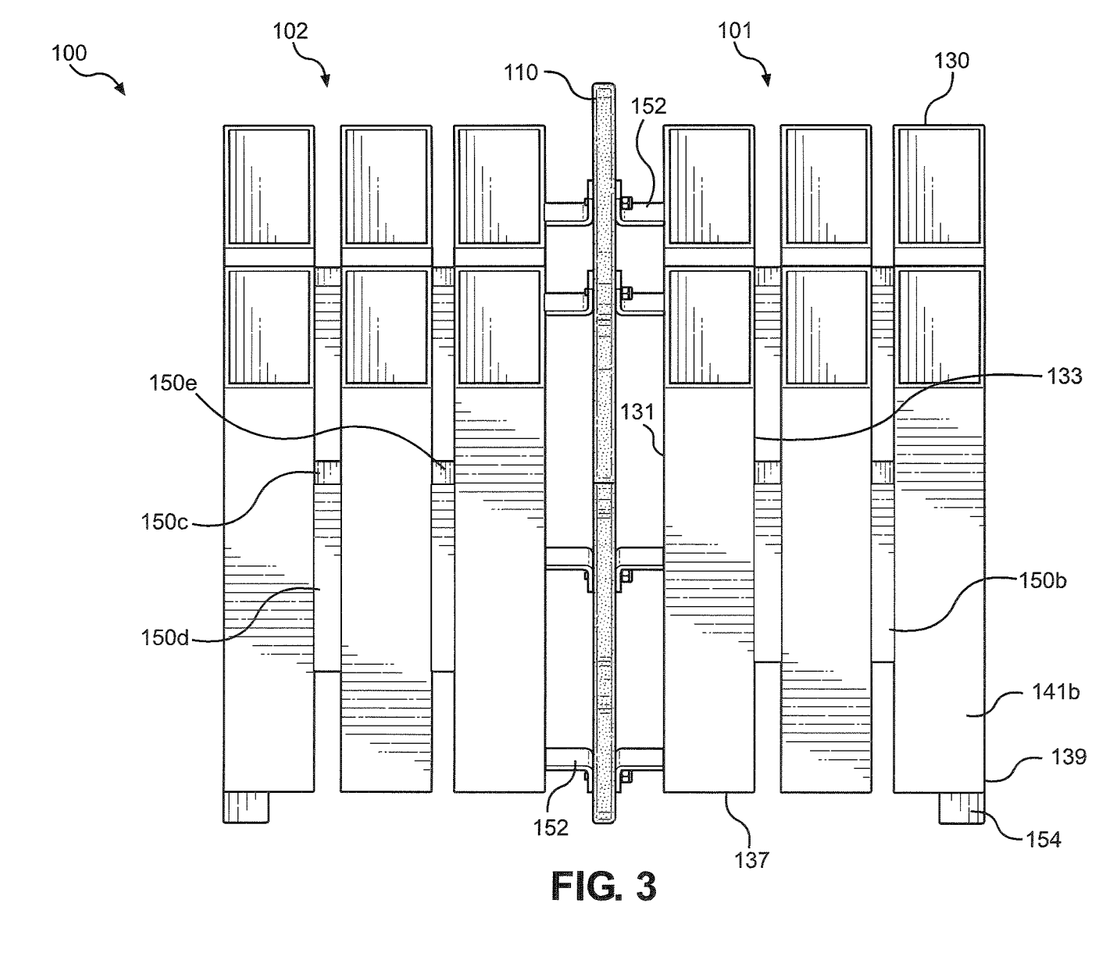
FIG. 3 is a top-left perspective view of the Thermally Isolated Blood Carrier Tray showing a plurality of individual thermally isolated compartments to house storage units.
Figure 4:
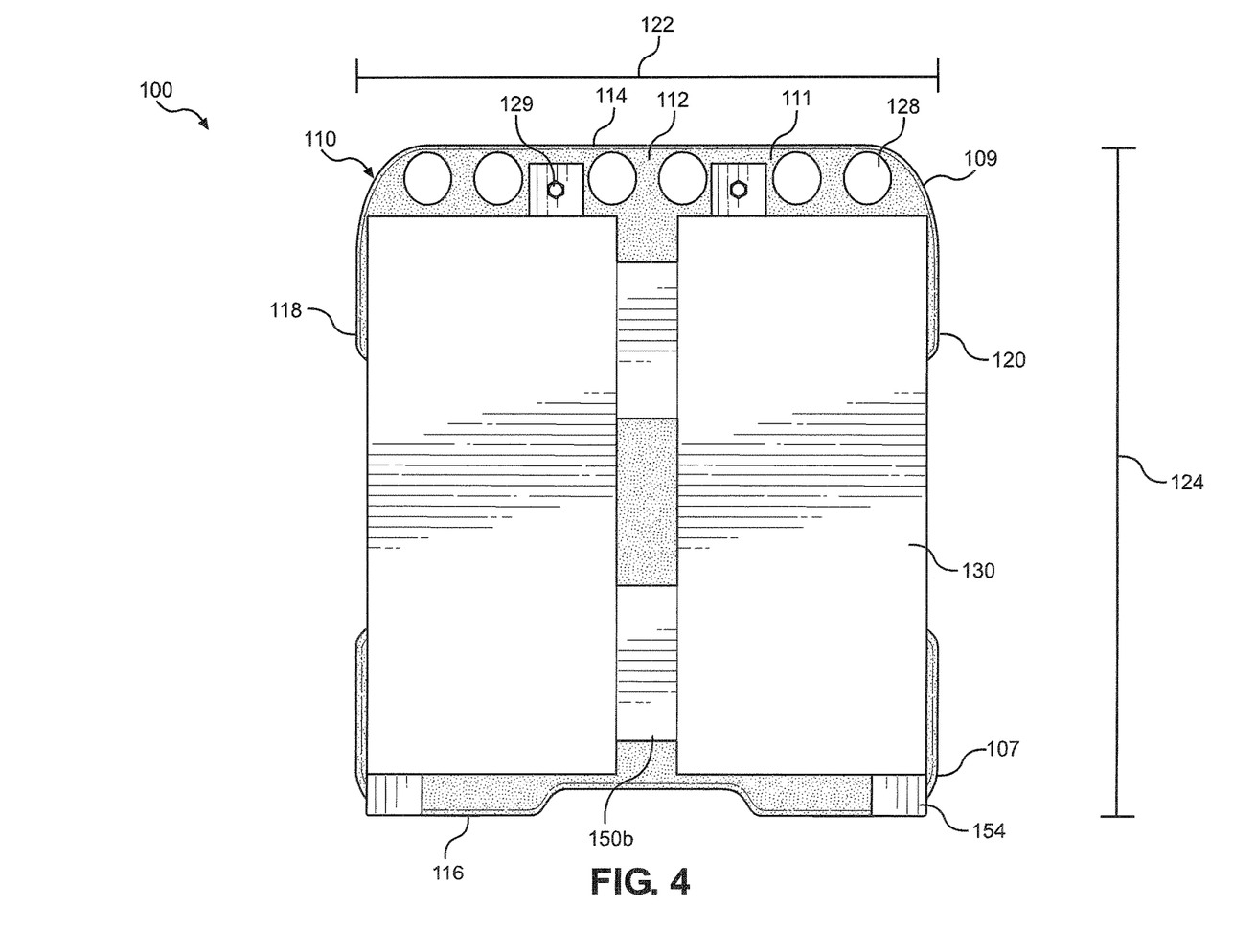
FIG. 4 is a front elevational view of the Thermally Isolated Blood Carrier Tray showing the thermally isolated compartments elevated by the feet of the thermally isolated compartments.
Figure 5:
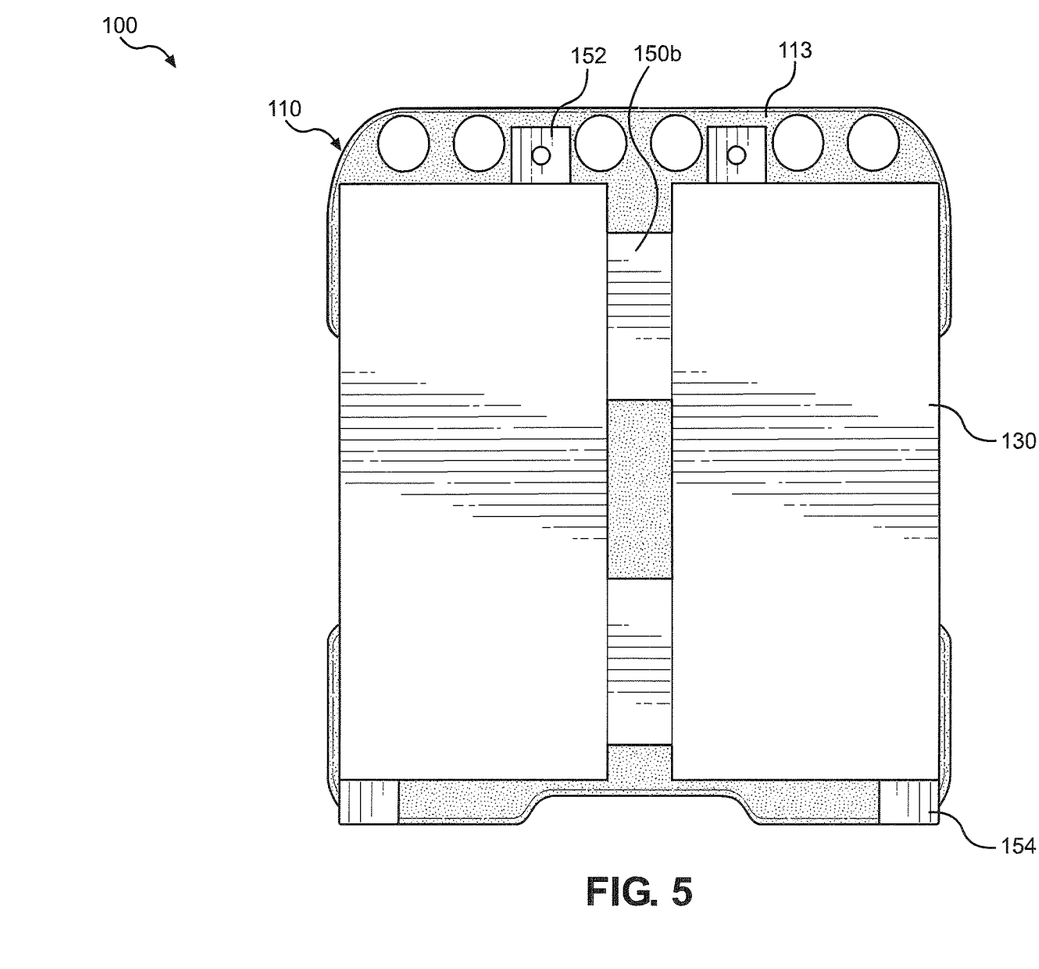
FIG. 5 is a back elevational view of the Thermally Isolated Blood Carrier Tray.
Figure 6:
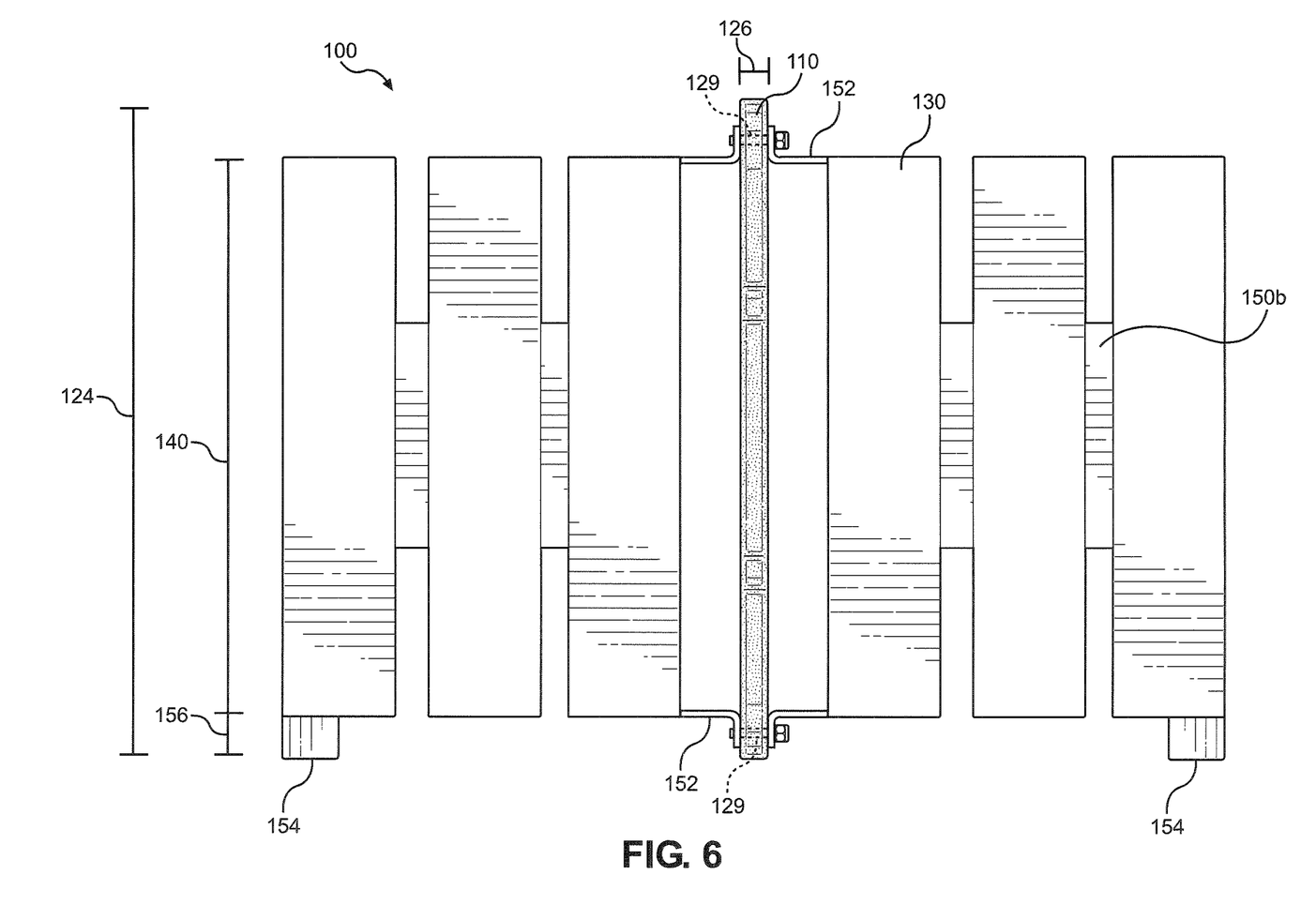
FIG. 6 is a left side elevational view of the Thermally Isolated Blood Carrier Tray showing the thermally isolated compartments elevated by the feet of the thermally isolated compartments.
Figure 7:
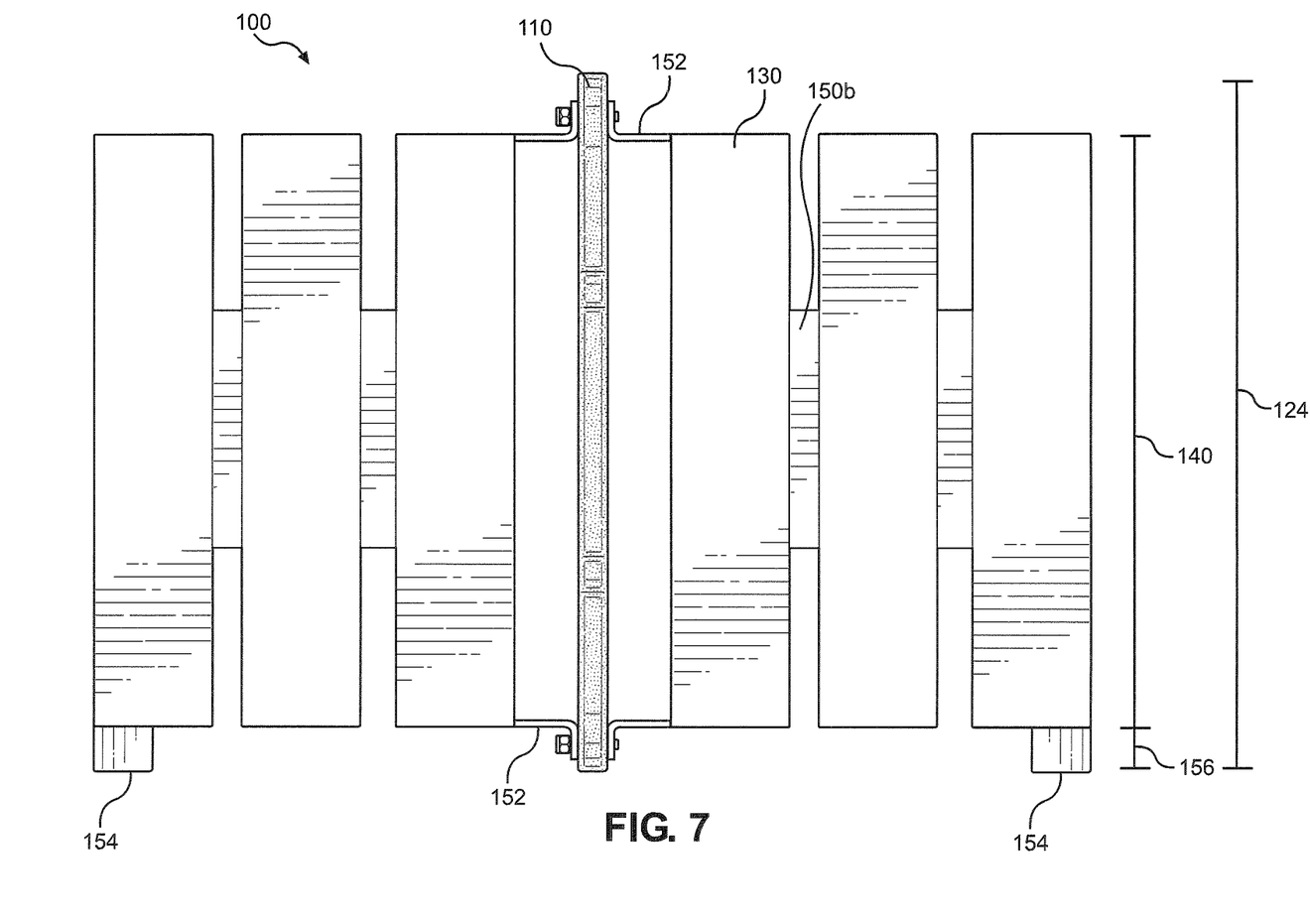
FIG. 7 is a right side elevational view of the Thermally Isolated Blood Carrier Tray.
Figure 8:
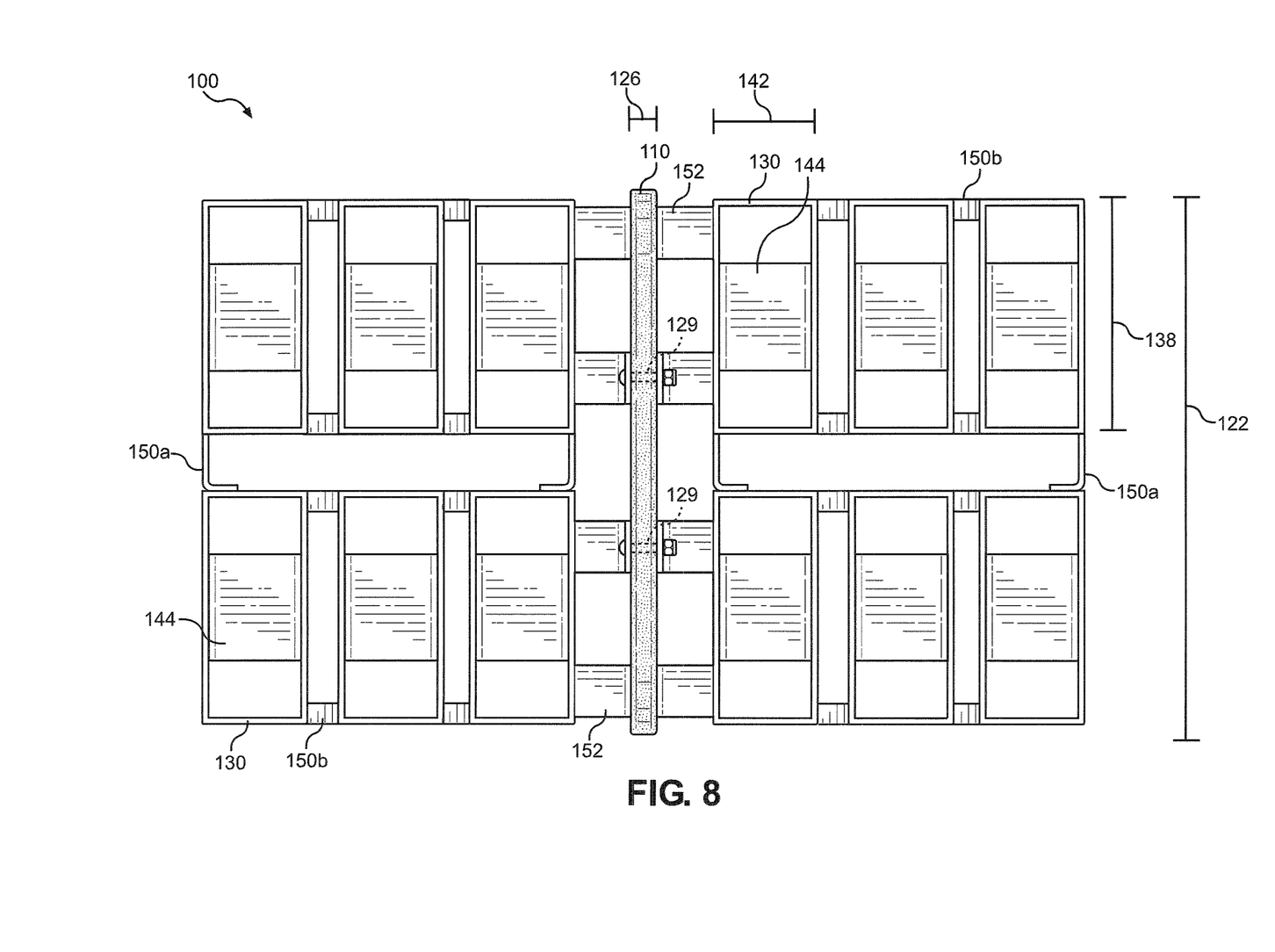
FIG. 8 is a top plan view of the Thermally Isolated Blood Carrier Tray.
Figure 9:
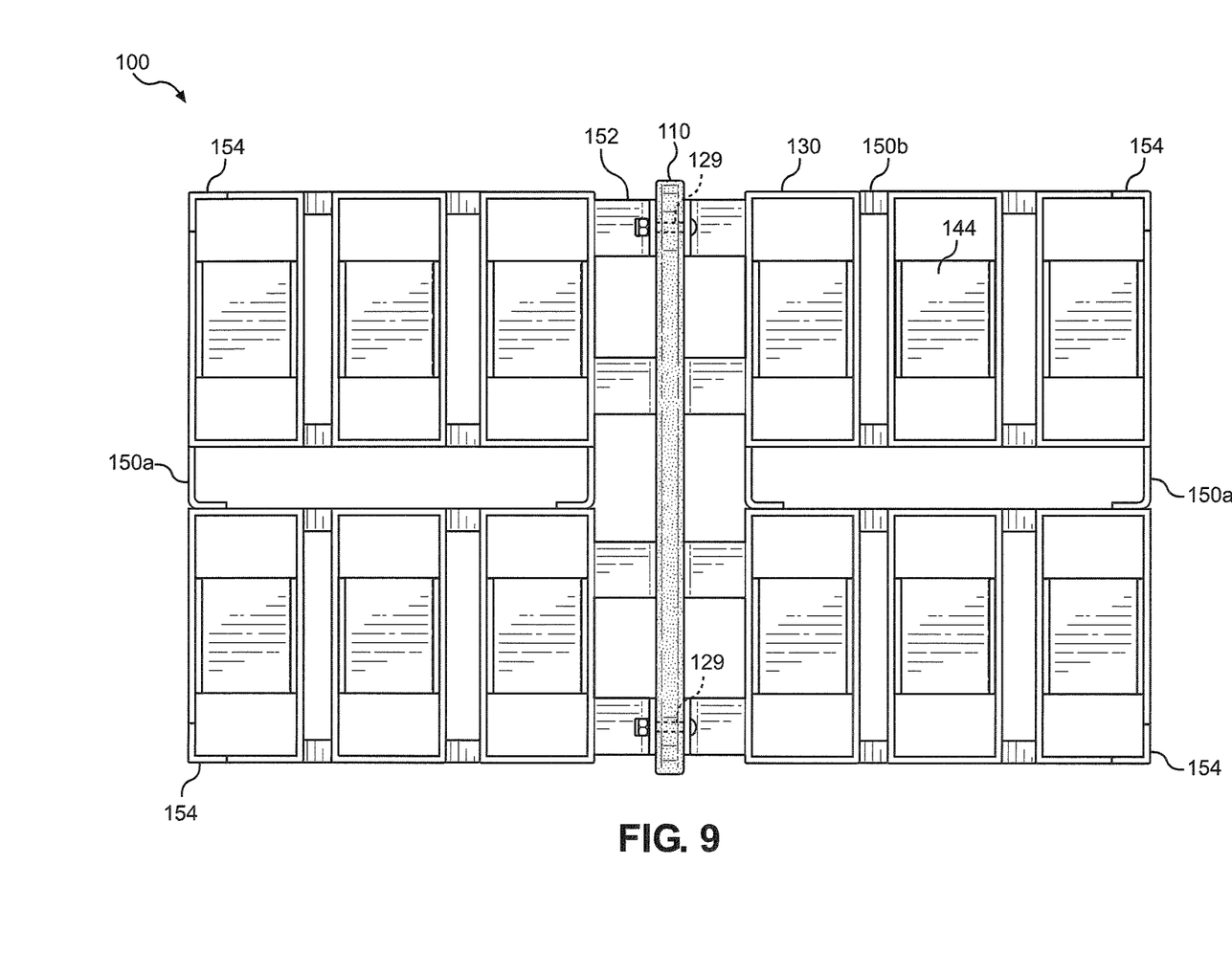
FIG. 9 is a bottom plan view of the Thermally Isolated Blood Carrier Tray.

The Thermally Isolated Blood Carrier Tray 100 provides a steady and even heat transfer from a whole blood storage unit, a red cell storage unit, a platelet storage unit, a plasma storage unit, or a cryoprecipitate storage unit (hereinafter referred collectively as "storage unit 200") to bring the storage units 200 to an appropriate temperature for storage or transportation. The Thermally Isolated Blood Carrier Tray 100 is capable of cooling multiple storage units 200 simultaneously without affecting the heat transfer rates of the other storage units 200. Each thermally isolated compartment 130 is thermally isolated from an adjacent thermally isolated compartment 130. In a preferred embodiment, the first row (103) and the second row (105) of the first (101) and second matrix (102) have thermally isolated compartments (130) in a first position (115), a middle position (117), and an end position (119). Each thermally isolated compartment 130 and the storage unit 200 housed within maintains its own heat transfer rate without being affected by an adjacent thermally isolated compartment 130 and the storage unit 200. The placement of several different storage units 200 having different temperatures into the Thermally Isolated Blood Carrier Tray 100 does not affect the heat transfer rate of any one storage unit 200 inserted into a thermally isolated compartment 130. The Thermally Isolated Blood Carrier Tray 100 allows for the placement of storage units 200 having different temperatures into the Thermally Isolated Blood Carrier Tray 100 at different times to lower its temperature to an appropriate temperature without the need to determine the effects it would have on the overall heat transfer rate.

In a preferred embodiment, described in conjunction with FIGS. 4-9, the thermally isolated compartments 130 are each formed from a rectangular tubing 132 having a first side 131, a second side 133, an inner side 141a, an outer side 141b, an open top side 134, an open bottom side 136, an outer edge 139, and an interior 127. The use of rectangular tubing 132 is not meant to be limiting, and it is contemplated that different shaped tubing or other structure may be used for the thermally isolated compartment 130. The thermally isolated compartments 130 are configured to have a length 138, height 140, and width 142 to accommodate the dimensions of the storage unit 200. A base 144 is mounted within the rectangular tube 132 to provide a resting platform 145 between a first side 143 and a second side 147 to prevent the storage unit 200 from passing through the rectangular tube 132 and to provide a platform that the storage unit 200 may rest. The base 144 is sized smaller than the opening of the rectangular tube 132 to provide open areas for the purpose of draining excess condensation. As the storage unit 200 is placed within the thermally isolated compartment 130, it makes physical contact with the rectangular tube 132 and the base 144. The low temperature of the storage unit 200 will cause condensation to form on the surface of the storage unit 200 and the thermally isolated compartment 130. The openings allow the condensation to drain and prevent the fluid from collecting on the bottom of the rectangular tubing 132.

In an alternative embodiment, the base 144 may completely seal the open bottom end 136 of the rectangular tube 132. This will allow the insertion of a thermally conductive fluid into the rectangular tube 132 for use as an interface between the storage unit 200 and the thermally isolated compartment 130. By using a thermally conductive fluid, such as water, as an interface between the storage unit 200 and the thermally isolated compartment 130 better heat conduction is made between the two. This provides increased thermal conductivity for the storage unit 200 by providing a larger surface area, by way of the conductive fluid and thermally isolated compartment 130, for the storage unit 200 to absorb or emit heat.

In the preferred embodiment, the thermally isolated compartments 130 are constructed from aluminum for its mechanical and heat transfer properties. The use of aluminum is not meant to be limiting, and it is contemplated that various other materials having similar mechanical and heat transfer properties may be used. The mechanical properties of aluminum allow the thermally isolated compartments 130 to hold its structural shape. The high thermal conductivity of aluminum allows the thermally isolated compartments 130 to conduct heat at a high rate; it allows the heat transfer between the cooled air and the storage unit 200 at a higher rate than materials having a lower thermal conductivity. The storage unit 200 is in physical contact with the thermally isolated compartment 130, which acts as a conductive radiator to provide more surface area to the storage unit 200 for heat to transfer between the storage unit 200 and the cooled air. Due to the large surface area and volume of the thermally isolated compartment 130, the overall rate of heat transfer between the storage unit 200 and the cooled air is increased.

Each thermally isolated compartment 130 is oriented vertically lengthwise and is attached to an adjacent thermally isolated compartment 130 with a bracket 150a or 150b, thereby creating a matrix of thermally isolated compartments 101 and 102. The bracket 150a and 150b also serves to space each of the thermally isolated compartments 130 apart. The brackets 150a and 150b are configured to minimize the amount of contact surface area and volume between each of the thermally isolated compartments 130 to minimize the amount of heat transfer between the compartments. This allows each of the thermally isolated compartments 130 to be at different temperatures without affecting the temperature of an adjacent thermally isolated compartment 130.

In the preferred embodiment, the brackets 150a and 150b are made of aluminum, the same material as the thermally isolated compartments 130. The brackets 150a and 150b have a first end 150c, middle portion 150d, and a second end 150e. The use of aluminum for the brackets 150a and 150b provides for ease of manufacturing and assembly. However, it is contemplated that the brackets 150a and 150b may be made of dissimilar materials from the thermally isolated compartments 130. It is contemplated that a material having a lower thermal conductivity than aluminum with similar mechanical properties may be used such as different metals, plastics, and composite materials, without departing from the spirit and scope of the invention.

The surrounding cooled air provides a continual and steady sink for heat. The spacing between the thermally isolated compartments 130 allows cooled air to continuously flow around the thermally isolated compartments 130 to provide constant and steady heat transfer between the storage units 200, the thermally isolated components 130, and the cooled air. The vertical orientation of each compartment 130 provides for the natural exchange of heated air rising from the compartment to be replaced with cooler air from below. This natural convection facilitates the cooling of a storage unit.

The brackets 150a and 150b minimizes the amount of heat transfer between each thermally isolated compartment 130, thereby ensuring the temperature of a thermally isolated compartment 130 does not affect an adjacent thermally isolated compartment 130.

Each matrix 101 and 102 is attached to either side of the main panel 110.

Attached to the thermally isolated compartment 130 adjacent the main panel 110 of each matrix of thermally isolated compartments 101 and 102 are mounting tabs 152 having a first end 152a and a second end 152b that allow each matrix of thermally isolated compartments 101 and 102 to mount to the main panel 110. Attached to the thermally isolated compartment 130 of each matrix of thermally isolated compartments 101 and 102 are feet 154 having a height 156 to space the Thermally Isolated Blood Carrier Tray 100 from a surface. The feet 154 have a first side 151 and a second side 152.

The main panel 110, described in conjunction with FIGS. 4-9, is made of a material having a low thermal conductivity. The material has strong mechanical properties which make it rigid and durable. The main panel 110 may be, but is not exclusively, made of plastics, wood, or metals formed with an insulation layer, or any other material or combination of materials having strong mechanical properties with a low thermal conductivity. The main panel 110 is formed from a sheet 112 having a rectangular shape with curved edges. The sheet 112 has a first side 111, a second side 113, a top side 109, a bottom side 107, a top edge 114, a bottom edge 116, a left edge 118, and a right edge 120. The sheet 112 has a length 122, a height 124, and a width 126. Adjacent the top edge 114 of the sheet 112, a handle 128 is provided in the form of a plurality of circular cut outs. It is contemplated that any other shape may be used for the cut out, where the cut outs allow for the handling of the Thermally Isolated Blood Carrier Tray 100. Further formed into the sheet 112 adjacent the top edge 114 and the bottom edge 116 are mounting points 129. The mounting points 129 are utilized to mount the first matrix of thermally isolated compartments 101 and second matrix of thermally isolated compartments 102 to the main panel 110.

In an alternative embodiment of the Thermally Isolated Carrier Tray 100, the main panel 110 and the thermally isolated compartments 130 are each removably attached to one another thereby allowing for the scaling of the Thermally Isolated Carrier Tray 100 to fit various size needs. Each thermally isolated compartment 130 is removably attached to an adjacent thermally isolated compartment 130 where bracket 150a and 150b are made to be removable. Brackets 150a and 150b may be attached with screws, nuts and bolts, latches, mechanical joints or various other means of removable attachment. The removable attachment of the thermally isolated compartment 130 allows for the scalability of the matrix of thermally isolated compartments 101 and 102. The matrix of thermally isolated compartments 101 and 102 may be configured to have as many rows and columns to fit a desired workplace. The Thermally Isolated Carrier Tray 100 may be modified to have numerous main panels 110 to provide additional structural support and thermal isolation as needed between each matrix of thermally isolated compartments.

While the Thermally Isolated Carrier Tray 100 of the present invention as herein shown and disclosed in detail is fully capable of obtaining the objects and providing the advantages herein before stated, it is to be understood that it is merely illustrative of preferred and alternative embodiments of the invention and that no limitations are intended to the details of construction or design herein shown other than as described in the appended claims.

I claim:

1. A thermally isolated blood carrier comprising:
 a plurality of thermally isolated compartments thermally isolated from one another, each of the plurality of thermally isolated compartments comprising
  a rectangular tube having a top open end and a bottom open end,
  a base smaller than the bottom open end and mounted to the bottom open end of the rectangular tube, resulting in open areas configured to drain excess condensation, and
  one or more brackets extending outward from the rectangular tube,
 wherein the one or more brackets is attached to an adjacent thermally isolated compartment of the plurality of thermally isolated compartments, and
 wherein the plurality of thermally isolated compartments are constructed out of aluminum.

2. The thermally isolated blood carrier tray of claim 1, wherein the one or more brackets have a lower thermal conductivity than the plurality of thermally isolated compartment.

3. The thermally isolated blood carrier tray of claim 1, wherein each of the plurality of thermally isolated compartment are spaced apart by the one or more brackets.

4. The thermally isolated blood carrier tray of claim 1, wherein the thermally isolated blood carrier further comprises a handle comprising a plurality of circular cutouts in a sheet centered in the plurality of thermally isolated compartments.

5. The thermally isolated blood carrier tray of claim 1, wherein the thermally isolated blood carrier further comprises a plurality of feet.

6. A thermally isolated blood carrier tray comprising:
 a first matrix of thermally isolated compartments;
 a second matrix of thermally isolated compartments; and
 a thermally insulated main panel with the first matrix of thermally isolated compartments attached to a first side of the thermally insulated main panel and the second matrix of thermally isolated compartments attached to a second side of the thermally insulated main panel,
 wherein the thermally insulated main panel is vertically oriented and forms a barrier between the first matrix of thermally isolated compartments and the second matrix of thermally isolated compartments, and
 wherein the first matrix of thermally isolated compartments and the second matrix of thermally isolated compartments are constructed out of aluminum.

7. The thermally isolated blood carrier tray of claim 6, wherein each thermally isolated compartment of the first matrix of thermally isolated compartments and the second matrix of thermally isolated compartments is configured to receive a storage unit.

8. The thermally isolated blood carrier tray of claim 6, wherein each thermally isolated compartment of the first matrix of thermally isolated compartments and the second matrix of thermally isolated compartments is thermally isolated from the other thermally isolated compartments of the first matrix of thermally isolated compartments and the second matrix of thermally isolated compartments.

9. The thermally isolated blood carrier tray of claim 6, wherein the first matrix of thermally isolated compartments are thermally isolated from the second matrix of thermally isolated compartments.

10. The thermally isolated blood carrier tray of claim 6, wherein a heat transfer rate of each of the thermally isolated compartments of the first matrix of thermally isolated compartments and the second matrix of thermally isolated compartments are insulated from the other thermally isolated compartments of the first matrix of thermally isolated compartments and the second matrix of thermally isolated compartments.

11. A thermally isolated blood carrier comprising:
 a plurality of first thermally isolated compartments;
 a plurality of second thermally isolated compartments;
 a thermally insulated main panel with the plurality of first thermally isolated compartments attached to a first side of the thermally insulated main panel and the plurality of second thermally isolated compartments attached to a second side of the thermally insulated main panel,
 wherein the thermally insulated main panel is vertically oriented and forms a barrier between the plurality of first thermally isolated compartments and the plurality of second thermally isolated compartments, and
 wherein the plurality of first thermally isolated compartments and the plurality of second thermally isolated compartments are constructed out of aluminum.

12. The thermally isolated blood carrier of claim 11, wherein each of the plurality of first thermally isolated compartments comprises:
 a rectangular tube having a top open end and a bottom open end,
 a base mounted to the bottom open end of the rectangular tube, and
 one or more brackets extending outward from the rectangular tube, wherein the one or more brackets is attached to an adjacent thermally isolated compartment of the plurality of first thermally isolated compartments.

13. The thermally isolated blood carrier of claim 12, wherein the plurality of first thermally isolated compartments are arranged into columns and rows.

14. The thermally isolated blood carrier of claim 13, wherein the one or more brackets space each of the plurality of first thermally isolated compartments into the columns and the rows.

15. The thermally isolated blood carrier of claim 14, wherein each of the plurality of second thermally isolated compartments comprises:
 a rectangular tube having a top open end and a bottom open end,
 a base mounted to the bottom open end of the rectangular tube, and
 one or more brackets extending outward from the rectangular tube, wherein the one or more brackets is attached to an adjacent thermally isolated compartment of the plurality of second thermally isolated compartments.

16. The thermally isolated blood carrier of claim 15, wherein the plurality of second thermally isolated compartments is arranged into columns and rows.

17. The thermally isolated blood carrier of claim 16, wherein the one or more brackets space each of the plurality of second thermally isolated compartments into the columns and the rows.

18. The thermally isolated blood carrier tray of claim 17, wherein each of the plurality of first thermally isolated compartments are thermally isolated and each of the plurality of the second thermally isolated compartments are thermally isolated.

19. The thermally isolated blood carrier tray of claim 17, wherein the plurality of first thermally isolated compartments is thermally isolated from the plurality of second thermally isolated compartments.

20. The thermally isolated blood carrier tray of claim 17, wherein the plurality of first thermally isolated compartments and the plurality of second thermally isolated compartments are each thermally isolated.

* * * * *